United States Patent

Drost et al.

Patent Number: 6,036,645
Date of Patent: Mar. 14, 2000

[54] ULTRASONIC PROBE

[75] Inventors: Cornelis Drost; Yuri Shkarlet; Andrey Kopychev; Lauren Ostergren; Irina Sergeeva, all of Ithaca, N.Y.

[73] Assignee: Transonic Systems, Inc., Ithaca, N.Y.

[21] Appl. No.: 09/054,615

[22] Filed: Apr. 3, 1998

Related U.S. Application Data

[63] Continuation-in-part of application No. 29/082,477, Jan. 23, 1998.

[51] Int. Cl.⁷ ................................. A61B 8/00; A61B 8/06
[52] U.S. Cl. ........................................... 600/459; 600/465
[58] Field of Search .................................. 600/459, 585, 600/589, 462, 463, 465; 607/101–102; 606/40, 41

[56] References Cited

U.S. PATENT DOCUMENTS

| | | | |
|---|---|---|---|
| 4,058,001 | 11/1977 | Waxman | 600/443 |
| 4,444,197 | 4/1984 | Koyano et al. | 600/443 |
| 4,677,756 | 7/1987 | Simon et al. | 600/589 |
| 4,823,809 | 4/1989 | Gott, Jr. et al. | 600/589 |
| 4,945,896 | 8/1990 | Gade | 600/504 X |
| 5,204,622 | 4/1993 | MasCaslin et al. | 324/220 |
| 5,318,525 | 6/1994 | West et al. | 600/585 |
| 5,325,855 | 7/1994 | Daghighian et al. | 600/585 |
| 5,398,689 | 3/1995 | Connor et al. | 128/662.03 |
| 5,469,853 | 11/1995 | Law et al. | 128/662.06 |
| 5,552,394 | 9/1996 | Zurbrugg | 128/662.06 |
| 5,647,367 | 7/1997 | Lum et al. | 128/662.06 |
| 5,782,828 | 7/1998 | Chen et al. | 607/102 X |
| 5,888,198 | 3/1999 | Eggers et al. | 604/114 |

*Primary Examiner*—Francis J. Jaworski
*Attorney, Agent, or Firm*—Brown, Pinnisi & Michaels, P.C.

[57] ABSTRACT

A probe includes a handle, neck, and sensor head. The neck consists of a stiff portion and a flexible portion. The neck is offset from the handle so that a hand of a surgeon holding the handle does not block the surgeon's view of sensor head. In another embodiment, the stiff portion includes three sections that have separate and distinct linear axes. The extended axis of the section adjacent the handle intersects the juncture of the flexible portion and the stiff portion of the neck, while the sensor head is connected to the flexible portion of the neck. The precise alignment of the handle and neck enables the precise placement of the sensor head around a small blood vessel.

4 Claims, 3 Drawing Sheets

ULTRASONIC PROBE

FIELD OF THE INVENTION

This application is a continuation in part of application Ser. No. 29/082,477 filed on Jan. 23, 1998. The invention pertains to the field of probes. More particularly, the invention pertains to an ultrasonic probe used to measure blood flow in arteries and veins exposed during surgery.

BACKGROUND OF THE INVENTION

Ultrasonic probes are used in many medical applications. Probes typically include a probe head and a connecting cable that attaches to a processing unit via a connector, along with an optional handle and neck. The probe head contains the ultrasound transducers and reflectors, with wiring from the probe head carried inside the neck and handle to an external location. The wiring typically includes wires for electric power and wires to carry signals from the probe head to the processing unit such as a computer.

A number of medical applications require specialized probes that can be manipulated and directed by the treating physician. For example, U.S. Pat. No. 5,204,622 (McCaslin et al.) discloses a tube inspection probe with a flexible cable which helically moves the probe head assembly through the tube. The patent discloses a mechanism for maintaining the axis of rotation of the cable in alignment with the center of the tube.

U.S. Pat. No. 5,647,367 (Lum et al.) discloses an ultrasonic probe for imaging tissues from inside a patient's body cavity. The probe includes a housing near the probe's distal end which is connected to a pivotable part of an ultrasonic beam emitting assembly. The pivotable part is pivoted through a driver, located near the ultrasound transducer, such that as the pivotable part pivots, it sweeps ultrasonic energy over a selected angle.

U.S. Pat. No. 5,522,394 (Zurbrugg) discloses an implantable ultrasonic probe for measuring the flow velocity of blood in humans and animals. The probe is shaped like a double handled tennis racket (one handle on each side of the head) with the blood vessel running perpendicular to the plane of the racket where the strings of the racket would be.

U.S. Pat. No. 5,469,853 (Law) discloses a bendable ultrasonic probe and sheath used for endosurgical operations. The probe consists of a rigid handle with a bendable section extending straight from the handle. The handle and bendable section are coaxial when the bendable section is not bending.

U.S. Pat. No. 5,398,689 (Conner et al.) discloses an ultrasonic probe assembly which includes a sensor head located at the tip of a flexible shaft. The flexible shaft is attached to and coaxial with a fixed shaft and connected handle.

The prior art generally falls into two categories: a pivotable head on the end of a shaft so that an ultrasound transducer can be rotated in different directions, or a head on a flexible portion that is connected to a fixed straight portion that extends straight out from a handle. There exists a need for a probe designed such that a relatively small sensor head at the tip of the probe can be inserted easily into deep surgical access openings so that the surgeon's hand holding the handle does not occlude the surgeon's view while precisely locating the sensor head around a small blood vessel.

SUMMARY OF THE INVENTION

Briefly stated, a probe includes a handle, neck, and sensor head. The neck consists of a stiff portion and a flexible portion. The neck is offset from the handle so that a hand of a surgeon holding the handle does not block the surgeon's view of the sensor head. In another embodiment, the stiff portion includes three sections that have separate and distinct linear axes. The extended axis of the section adjacent the handle intersects the juncture of the flexible portion and the stiff portion of the neck, while the sensor head is connected to the flexible portion of the neck. The precise alignment of the handle and neck enables the precise placement of the sensor head around a small blood vessel.

According to an embodiment of the invention, a probe includes a neck, wherein the neck includes a stiff portion and a flexible portion; the stiff portion includes first, second, and third sections having first, second, and third lengthwise axes, respectively, the first, second, and third axes are non-collinear; the first axis, extended from an intersection of the first and second sections, intersects an end of the third section; the end of the third section being connected to a first end of the flexible portion of the neck; a handle connected to the first section of the stiff portion of the neck; and a sensor head connected to a second end of the flexible portion of the neck.

According to an embodiment of the invention, a probe includes a handle; a neck connected to the handle, the neck consisting of a stiff portion and a flexible portion; a sensor head connected to the flexible portion of the neck; the stiff portion including first, second, and third sections that have separate and distinct linear axes; the first section being to adjacent the handle; and an extended axis of the first section intersecting a juncture of the flexible portion and the stiff portion.

According to an embodiment of the invention, a probe includes a handle having a distinct handle axis; a neck consisting of a stiff portion and a flexible portion, wherein a first end of the stiff portion is connected to the handle, a second end of the stiff portion is connected to the flexible portion, and the stiff portion includes a distinct linear section adjacent the second end; a sensor head connected to the flexible portion of the neck; and the distinct linear section being offset from the handle such that an axis of the distinct linear section extended towards the handle is unobstructed by a hand holding the handle.

DESCRIPTION OF THE PREFERRED EMBODIMENT

Figure 1:
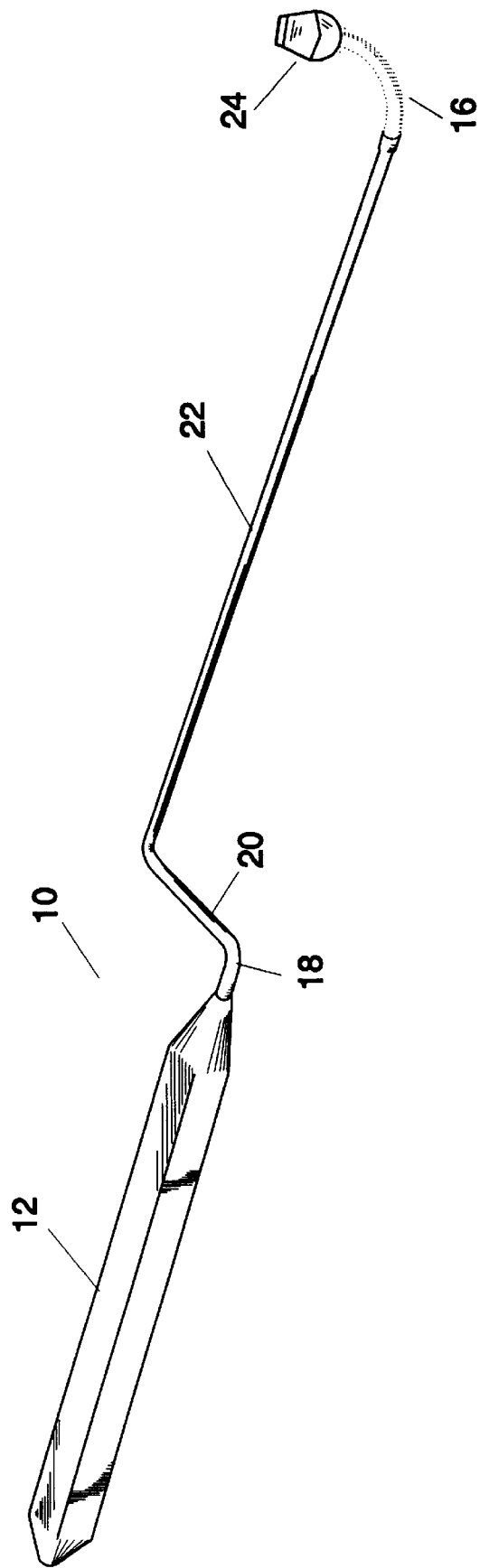
FIG. 1 shows a perspective view of a probe according to an embodiment of the present invention.

Referring to FIG. 1, a probe 10 includes a handle 12 that is shaped such that a person can easily hold on to it. Handle 12 is shown shaped as a triangular prism, but is optionally shaped as a circular or ellipsoid cylinder, rectangular prism, or a prism having five or more sides. The handle is preferably made of ABS or other bio-compatible plastic. A stiff portion 14 is connected to an end of handle 12, extending away from handle 12 a suitable distance. The distance between the end of handle 12 and the end of stiff portion 14 is determined by the medical/biological application using the probe and the size and type of sensor head attached. Stiff portion 14 is divided into first section 18, second section 20, and third section 22.

A flexible portion 16 is connected to the end of stiff portion 14. Flexible portion 16 is preferably of a flexible medical grade plastic or silicone which contains the connecting cable wires (not shown) plus a malleable guide wire that is flexible enough so the surgeon can position it with finger pressure, while being stiff enough so it holds its position once set. The guide wire may be a suitable strand of stainless steel or the like. Flexible portion 16 must also be strong enough to hold a sensor head 24 on its end. Sensor head 24 is preferably an ultrasound sensor such as found on the R, S, and V series probes manufactured by Transonic Systems, Inc. Flexible portion 16 is just long enough to permit bending to approximately a 90° angle from an axis of handle 12, thereby permitting movement of sensor head 24 in all directions.

Figure 2:
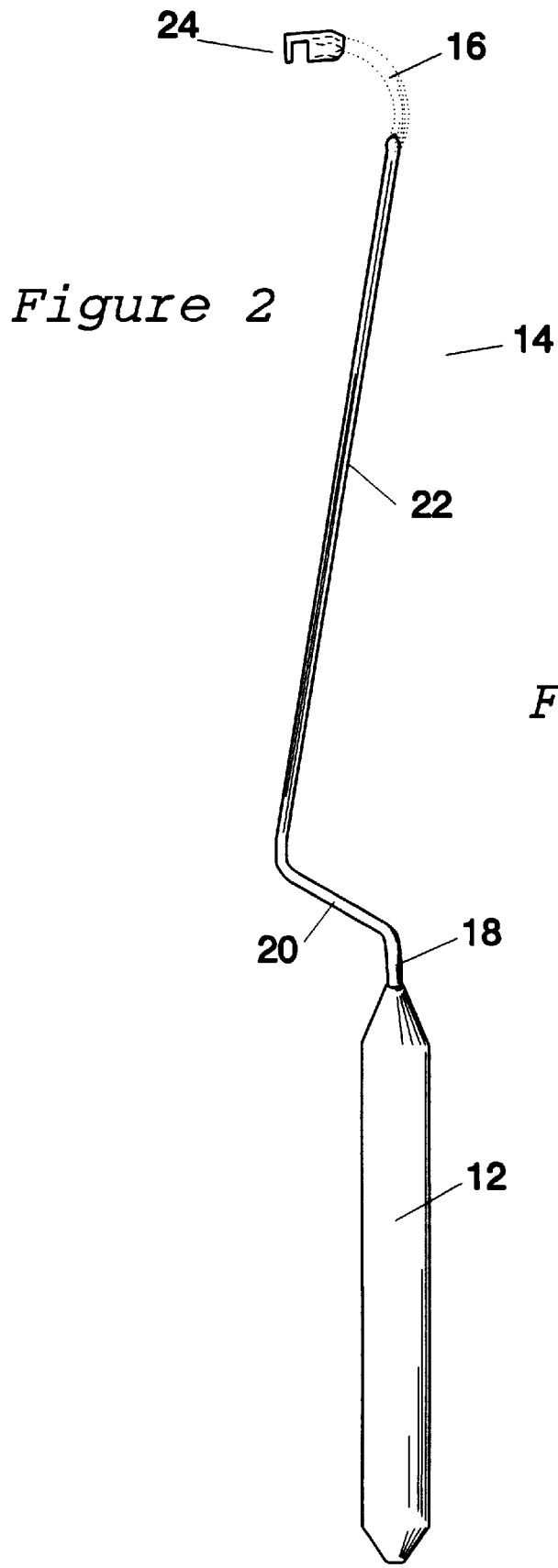
FIG. 2 shows a front elevation view of the probe of FIG. 1.

Referring to FIG. 2, first section 18 is preferably collinear with handle 12. Second section 20 is preferably longer than first section 18, meeting first section 18 at an angle preferably between 90° and 140°. Third section 22 is much longer than first and second sections 18, 20 since third section 22 has to be long enough to reach from a point of entry into a body to the location of the blood vessel being sensed by sensor head 24.

An extended axis of first section 18 preferably intersects probe 10 at the juncture of stiff portion 14 and flexible portion 16. This alignment enables precise placement of sensor head 24 around a small blood vessel or other tube. Sensor head 24 thus feels like an extension of handle 12 to a person holding probe 10, and rotating handle 12 rotates sensor head 24 in a predictable fashion.

Figure 3:
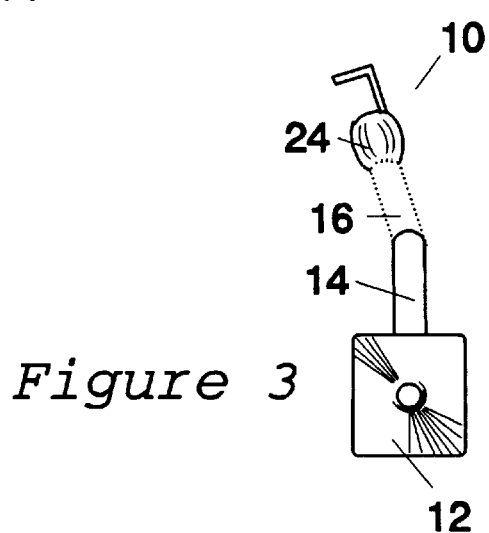
FIG. 3 shows a bottom view of the probe of FIG. 1.
Figure 4:
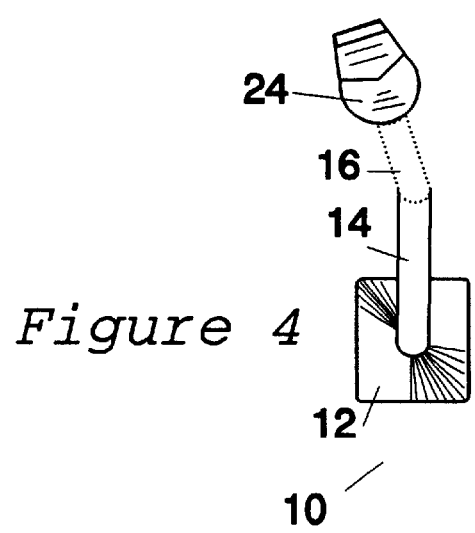
FIG. 4 shows a top view of the probe of FIG. 1.

Referring to FIGS. 3 and 4, the total lateral area of probe 10 is kept relatively small while providing the flexibility and versatility of this design. For example, in the preferred embodiment, handle 12 is approximately 93 mm long. First section 18 is approximately 4 mm, while second section 20 is approximately 25 mm. Third section 22 is approximately 100 mm, while flexible portion 16 is approximately 15 mm. With these dimensions, the angle between first section 18 and second section 20 is 130°, while the angle between second section 20 and third section 22 is 120°. The extension of the axis of handle 12 crosses probe 10 approximately at the juncture of stiff portion 14 and flexible portion 16. The visual line of sight between the eyes of the surgeon and probe head 24 is thus not occluded by the hand of the surgeon on handle 12.

Figure 5:
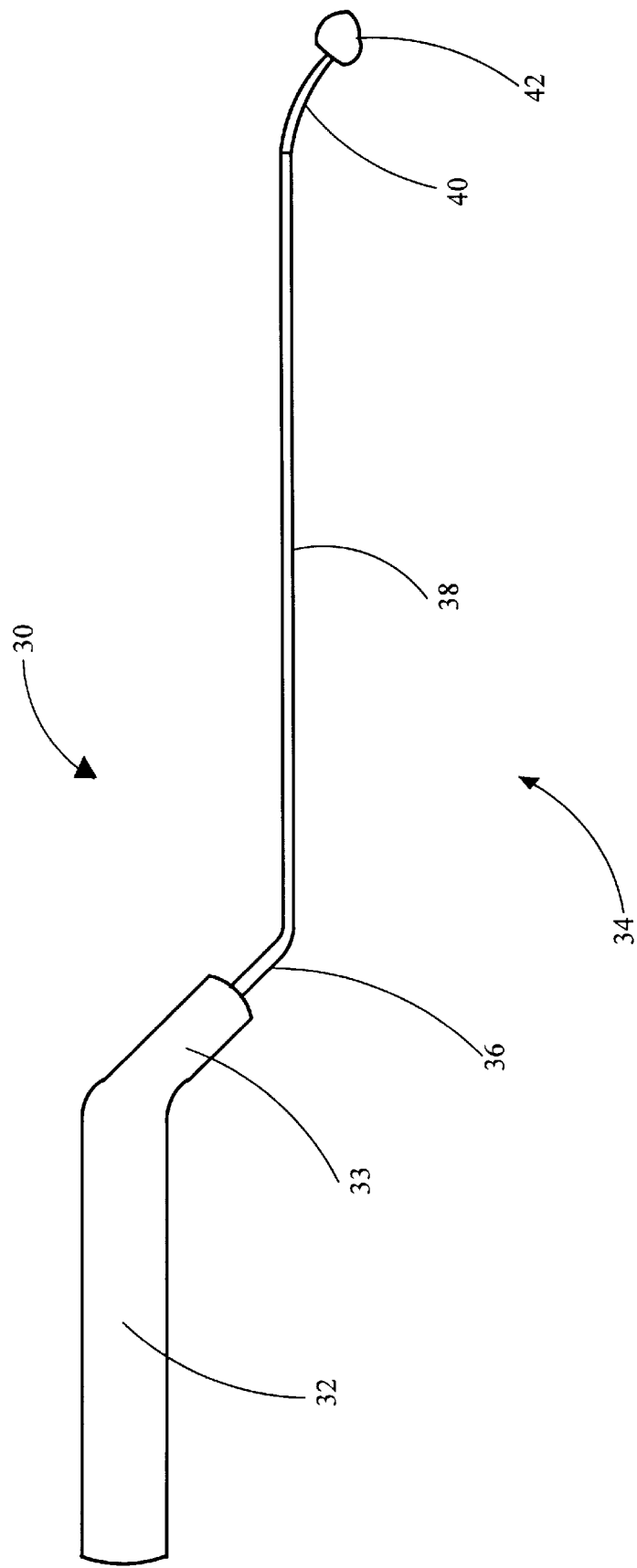
FIG. 5 shows a front elevation view of a probe according to an embodiment of the invention.

Referring to FIG. 5, a probe 30 includes a handle 32 with a bent handle portion 33 connected to a first stiff portion 36 of a neck 34. A second stiff portion 38 connected to first stiff portion 36 extends approximately 10 cm in a direction roughly parallel to handle 32. Second stiff portion 38 is connected to a flexible portion 40 which in turn is connected to a probe head 42. The offset provided by bent handle portion 33 and first stiff portion 36 is sufficient to ensure that a surgeon's hand holding handle 32 does not visually occlude probe head 42.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A handheld probe, comprising:

a) a neck, wherein
   i) said neck includes a stiff portion and a flexible portion;
   ii) said stiff portion includes first, second, and third sections having first, second, and third lengthwise axes, respectively;
   iii) said first, second, and third axes are non-collinear;
   iv) said first axis, extended from an intersection of said first and second sections, intersects an end of said third section;
   v) said end of said third section being connected to a first end of said flexible portion of said neck;

b) a handle connected to said first section of said stiff portion of said neck; and c) a sensor head connected to a second end of said flexible portion of said neck.

2. A handheld probe, comprising:

a handle;

a neck connected to said handle, said neck consisting of a stiff portion and a flexible portion;

a sensor head connected to said flexible portion of said neck;

said stiff portion including first, second, and third sections that have separate and distinct linear axes;

said first section being adjacent said handle; and an extended axis of said first section intersecting a juncture of said flexible portion and said stiff portion.

3. A handheld probe, comprising:

a handle having a distinct handle axis;

a neck consisting of a stiff portion and a flexible portion, wherein
   a first end of said stiff portion is connected to said handle,
   a second end of said stiff portion is connected to said flexible portion, and
   said stiff portion includes a distinct linear section adjacent said second end;

a sensor head connected to said flexible portion of said neck; and said distinct linear section being offset from said handle such that an axis of said distinct linear section extended towards said handle is unobstructed by a hand holding said handle.

4. A probe according to claim 3, wherein an extension of said distinct handle axis intersects said neck substantially where said stiff portion meets said flexible portion.

* * * * *